United States Patent
Gowda et al.

(10) Patent No.: US 6,459,917 B1
(45) Date of Patent: Oct. 1, 2002

(54) APPARATUS FOR ACCESS TO INTERSTITIAL FLUID, BLOOD, OR BLOOD PLASMA COMPONENTS

(76) Inventors: Ashok Gowda, 100 Redmond Dr., College Station, TX (US) 77840; Roger McNichols, 3715 Sweetbriar, Bryan, TX (US) 77802

( * ) Notice: Subject to any disclaimer, the term of this patent is extended or adjusted under 35 U.S.C. 154(b) by 0 days.

(21) Appl. No.: 09/575,591

(22) Filed: May 22, 2000

(51) Int. Cl.⁷ .................................................. A61B 8/00
(52) U.S. Cl. ...................... 600/345; 600/584; 600/576; 600/573; 604/175
(58) Field of Search ............................... 600/345, 347, 600/573, 578, 584; 604/175

(56) References Cited

U.S. PATENT DOCUMENTS

| | | |
|---|---|---|
| 3,638,649 A | 2/1972 | Ersek |
| 3,663,965 A | 5/1972 | Lee, Jr. et al. |
| 3,783,868 A * | 1/1974 | Bokros ..................... 604/891.1 |
| 3,991,756 A | 11/1976 | Synder |
| 4,402,694 A | 9/1983 | Ash et al. |
| 4,633,878 A | 1/1987 | Bombardieri |
| 4,777,953 A | 10/1988 | Ash et al. |
| 4,810,246 A * | 3/1989 | Frisch et al. ................... 604/93 |
| 4,854,322 A | 8/1989 | Ash et al. |
| 4,886,501 A | 12/1989 | Johnston et al. |
| 4,886,502 A | 12/1989 | Poirier et al. |
| 4,955,861 A * | 9/1990 | Eenegren et al. ........... 604/141 |
| 5,001,054 A | 3/1991 | Wagner |
| 5,035,711 A * | 7/1991 | Aoki et al. ..................... 623/11 |
| 5,161,532 A | 11/1992 | Joseph |
| 5,242,415 A | 9/1993 | Kantrowitz et al. |
| 5,568,806 A | 10/1996 | Cheney, II et al. |
| 5,582,184 A | 12/1996 | Erickson et al. |
| 5,617,851 A | 4/1997 | Lipkovker |
| 5,662,616 A | 9/1997 | Bousquet |
| 5,706,807 A | 1/1998 | Picha |
| 5,722,397 A * | 3/1998 | Eppstein ..................... 600/345 |
| 5,746,217 A | 5/1998 | Erickson et al. |
| 5,820,570 A | 10/1998 | Erickson et al. |
| 5,833,655 A * | 11/1998 | Freed et al. ..................... 604/93 |
| 5,885,211 A | 3/1999 | Eppstein et al. |
| 5,913,833 A | 6/1999 | Elstrom et al. |
| 5,964,804 A * | 10/1999 | Brauker et al. ................ 623/11 |
| 6,099,508 A * | 8/2000 | Bousquet ..................... 604/175 |
| 6,122,536 A | 9/2000 | Sun et al. |

OTHER PUBLICATIONS

Dasse et al., "A polyurethane percutaneous access device for peritoneal dialysis, Advances in Peritoneal Dialysis", 1988, 4: 245–252.

Kayashima et al., "New Noninvasive Transcutaneous Approach to Blood Glucose Monitoring: Successful Glucose Monitoring on Human 75 g OGTT with Novel Sampling Chamber" IEEE Trans. On Biomed. Eng., 1991, vol. 38(8), pp. 752–757.

Wood et al., "Assessment of a Model for Measuring Drug Diffusion Through Implant–Generated Fibrous Capsule Membranes", Biomaterials Journal, 1995, 16:957–9.

Padera, R. et al., "Time Course of Membrane Microarchitecture–driven Neovascularization", Biomaterials Journal, 1996, 17(3):277–84.

Petersen et al., "Microdialysis of the Interstitial Water Space in Human Skin In Vivo: Ouantitiative Measurement of Cutaneous Glucose Concentrations", Journal of Investigative Dermatology, 1992: 99–357–360.

* cited by examiner

*Primary Examiner*—Robert L. Nasser
(74) *Attorney, Agent, or Firm*—Neil A. Steinberg (57) ABSTRACT

A transcutaneous implant having a stable biological seal at the skin interface, obviating the need for puncturing the skin to obtain fluid samples is described. The implant includes an advanced filtration membrane to promote neovascularization which eliminates mass transfer problems by promoting the development of capillary networks with transcapillary mass transfer rates high enough to insure rapid exchange of analyte between blood and the device. Additionally the membrane provides a bioprotective layer which prevents transport of proteins and cellular components into the device.

58 Claims, 5 Drawing Sheets

APPARATUS FOR ACCESS TO INTERSTITIAL FLUID, BLOOD, OR BLOOD PLASMA COMPONENTS

BACKGROUND OF THE INVENTION

The invention is directed to an apparatus for intradermal implantation of a device to facilitate repeated, painless, safe, and reliable access to interstitial fluid, blood, or blood plasma for monitoring of blood borne or tissue analyte concentrations including but not limited to glucose, cholesterol, lactate, bilirubin, blood gases, ureas, creatinine, phosphates, myoglobin and hormones or delivery of drugs or other injectable agents such as chemotherapeutic agents, photosensitizing agents, hormones, vaccines, or radiological or other contrast agents.

There is now a large body of evidence that intensive management of blood sugars is an effective means to slow or even prevent the progression of diabetic complications such as kidney failure, heart disease, gangrene, and blindness. The design and development of a simple apparatus for obtaining interstitial fluid, blood or blood plasma samples without breaking the skin would be a large advancement in trying to improve diabetic patient compliance for monitoring blood glucose levels.

Maintaining blood glucose concentrations near normal levels in diabetic patients can only be achieved with frequent blood glucose monitoring so that appropriate actions can be taken, such as insulin injections, or sugar ingestion. Unfortunately the current methods of sensing are based on colorimetric or electro-enzymatic approaches that require a blood or interstitial fluid sample each time a reading is needed. Withdrawal of a blood or interstitial fluid sample currently requires invasive methods of penetrating the skin surface. These methods are both time-consuming and painful and therefore there is a significant lack of compliance among the diabetic population for monitoring their blood glucose levels for the recommended five or more times daily.

Several research groups have focused efforts on methods for minimally invasive withdrawal of (primarily) interstitial fluid including the use of electrical current, suction, penetration, microdialysis, and laser-assisted drilling of the stratum corneum. While these techniques have shown some preliminary promise, questions still remain as to the volume of fluid which can be obtained, the repeatability of samples obtained, and the lack of any significant improvement in skin trauma related to the sampling methods. Additionally, the accuracy of glucose measurements on such small samples of interstitial fluid will likely be highly sensitive to contaminants from sweat or dirt on the surfaces being sampled and requires development of new measurement technology appropriate for such small or low concentration samples. Therefore, the ability to directly withdraw interstitial fluid samples in an easy, reliable and safe manner would be a significant advance in minimally invasive sensing techniques.

Other groups are developing totally implantable sensors for measurement of blood or interstitial fluid glucose concentration. Normally, however, when a foreign body such as a medical implant is introduced into a host, the natural tendency of the surrounding tissue is to degrade or extrude the implant. If the host cannot eliminate the foreign body, a chronic inflammatory reaction results and the object is encapsulated in fibrous tissue with foreign body giant cells residing at the tissue-material interface. This capsule poses a difficult problem in the development of implanted sensing or sampling devices. In the case of interstitial fluid sampling, the fibrous capsule presents a mass transfer barrier and therefore limits the concentration of analyte reaching the collection site. Also, encapsulated implants may exhibit a significant lag time in the response to changes in blood glucose concentration. The ability of the capsule to limit mass transfer has been demonstrated in several studies (see, for example, Wood et al., Assessment of a Model for Measuring Drug Diffusion Through Implant-Generated Fibrous Capsule Membranes, *Biomaterials*. 16:957–9, (1995)).

SUMMARY OF THE INVENTION

In one aspect, the present invention is directed to a method and apparatus for analyte detection which substantially overcomes one or more of the problems due to the limitations and disadvantages of the related art. More specifically, in this aspect the present invention is directed to a transcutaneous implant, methods for implanting and using the transcutaneous implant and fluid withdrawal/delivery implements and replaceable components for use with the transcutaneous implant. In one embodiment of this aspect of the invention, the transcutaneous implant includes an access component to provide a stable dermal interface, a central housing disposed within the access component, a septum disposed within the central housing, and a filtration membrane disposed at a distal end of the central housing to promote mass transfer of analyte in bodily fluid into a reservoir formed by the filtration membrane, the septum and the central housing.

These and other features and advantages of the present invention will be apparent from the accompanying drawings and from the detailed description and claims that follow.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

The invention disclosed herein eliminates many of the problems associated with prior art methods for fluid withdrawal. In one embodiment, a transcutaneous implant is provided, obviating the need for puncturing the skin to obtain fluid samples. The implant promotes a stable biological seal at the skin interface and prevents capsule formation and exist site infection. The implant includes an advanced filtration membrane that eliminates the mass transfer problem by promoting capillary networks with transcapillary mass transfer rates high enough to ensure rapid exchange of analyte between blood and the device. There are several strategies for promoting this neovascularization, including prevascularization, the release of angiogenic factors, and microarchitecture-driven neovascularization.

Certain microporous materials allow blood vessels to grow and be maintained at the tissue-material interface and in some cases within the pores of the material. However this is not true for all porous polymer membranes, even those with similar porosities and chemistries. What influences the host response is not necessarily the chemistry of the material, but the microstructure of individual features within the material onto which host cells can attach. Materials that are microporous but contain large planar features promote an avascular host response while the same material lacking these planar features and having a more fibrous structure promote neovascularization at the tissue-material interface. Thus, in embodiments of the present invention, microporous polymers having a fibrous structure are integrated into the implanted transport membrane to reduce fibrosis and enhance neovascularization.

Figure 1A:
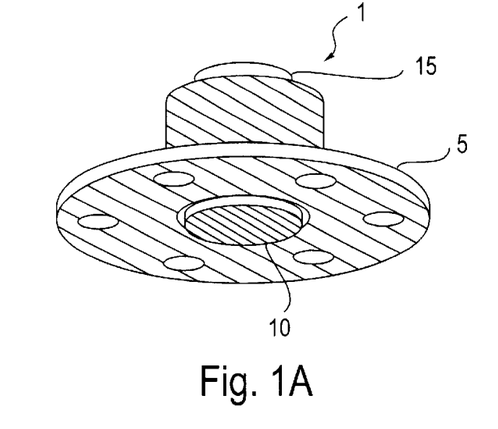
FIG. 1A is an elevational perspective side view of the implantable access port in accordance with one embodiment of the present invention.
Figure 1B:
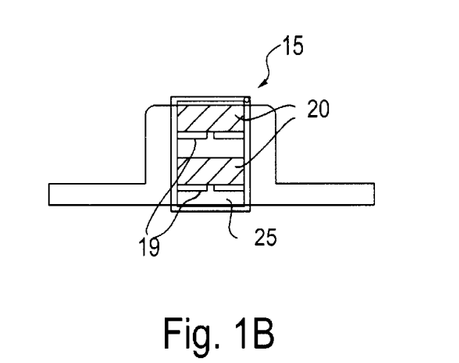
FIG. 1B is a cross-sectional view of the implantable access port shown in FIG. 1A.

An embodiment of the present invention is illustrated in FIGS. 1A–1E. As shown in FIGS. 1A and 1B, an implantable access port 1 includes three main components. First, implantable access port 1 includes an access component 5 for providing a stable dermal interface for the transcutaneous implant. Second, implantable access port 1 uses an advanced filtration membrane 10 engineered to promote improved mass transfer between analytes in the blood and those collected by implantable access port 1. Finally, a central housing 15 with septa 20 that form self-sealing apertures and a reservoir 25 for storage of fluid prior to collection is provided. Annular support members 19 are affixed to central housing 15 (or formed integrally with the central housing) to support and position septa 20.

Using needles, capillary tubes or other aspirating device, interstitial fluid, blood or blood plasma can be sampled from the access port 1 in a painless fashion since the skin at the exit site is effectively removed. Practice of this device by a diabetic patient would allow the patient to monitor blood glucose levels more frequently and maintain approximately normal 24-hour blood-glucose profiles thereby reducing complications related to the disease.

The preferred embodiments of this invention are described below. Alternate embodiments are listed as well. The design of the implantable access port 1 is based on providing a stable interface for the implant at an externally located site and incorporating a suitable membrane for long-term biocompatibility and filtration performance.

Access Component

Figure 1C:
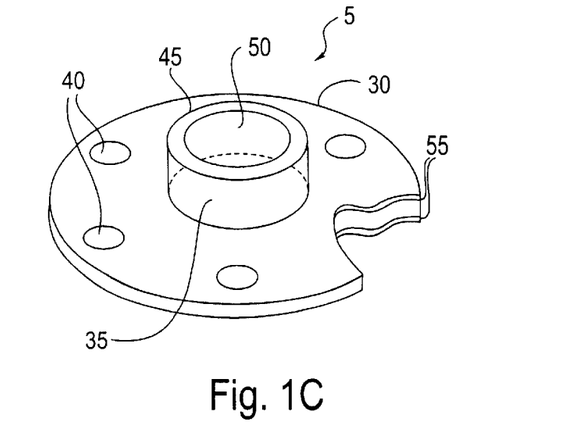
FIG. 1C is an elevational perspective side view of the transcutaneous access component according to one embodiment of the present invention.

The access component 5 shown in FIG. 1C includes a flat, disc-shaped skirt 30 having a central opening 35 and an array of through holes 40 distributed around disc-shaped skirt 30. Extending out from one side of skirt 30 in registration with the opening is an integral tubular neck 45 whose lumen 50 is in registration with the opening of skirt 30. The access component 5, including skirt 30 and neck 45, is preferably formed of a flexible, thermally stable, biocompatible material such as flexible medical grade polyurethane, polymethyl methacrylate (PMMA). polyethylene (PE), polyvinyl chloride (PVC), polycarbonate, polypropylene (PP) polydimethyl siloxane (PDMS), ethylene glycol dimethacrylate (EGDM), polytetrafluoroethylene PTFE), nylon or the like.

Preferably, the entire body of the skirt 30 and neck 45 is covered by a porous covering or bed 55 of material such as polyester velour (U.S. Catheter and Instrumentation Company of Glenfalls, N.Y. Part # 600k61121). In one embodiment, the thickness of the covering 55 preferably may range from 0.01 mm to 1.5 mm, and even more preferably is about 0.1 mm. The covering encourages cell infiltration and the formation of subcutaneous tissue and collagen. The overall design of the access component 5 may be as set forth in U.S. Pat. No. 5,662,616, which is hereby incorporated herein by reference.

In the present invention, skirt 30 preferably has a diameter ranging from 0.2 to 4.0 cm, even more preferably about 2.5 cm. The thickness of skirt 30 preferably may range from 0.05 to about 0.5 cm, and even more preferably is about 0.2 cm. The central opening of skirt 30 and lumen 35 of neck 45 preferably may range from 0.1 to 3.0 cm in diameter, and even more preferably are about 0.7 cm. The outer diameter of neck 45 preferably may range from 0.25 to 2.0 cm, and even more preferably is about 1.0 cm. The height of the entire access component 5 preferably ranges from about 0.25 to about 2.5 cm, and even more preferably is about 1.0 cm.

Advanced Filtration Membrane

Figure 1D:
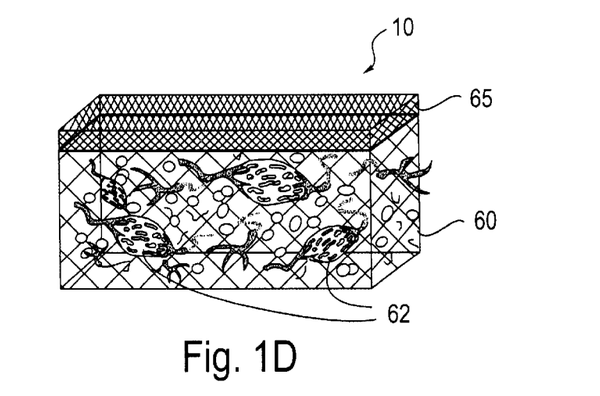
FIG. 1D is an elevational perspective side view of the advanced filtration membrane component of the present invention.

FIG. 1D illustrates the advanced filtration membrane 10 according to one embodiment. The membrane 10 is designed to allow for passive diffusion of analytes in interstitial fluid (ISF) while preventing transport of cells and larger proteins. The filtration membrane 10 is preferably constructed from a polyvinylidene fluoride (PVDF) membrane 60, although other materials may be used including, but not limited to, cellulose acetate, mixed esters of cellulose, polysulfone, polyester, polypropylene, cellulose nitrate, polycarbonate, nylon (charged and uncharged), polyethylene, and vinyl acetate ethylene copolymers. The PVDF membrane 60 is used to promote microachitecture-driven neovascularization 62. To prevent cells from entering the collection reservoir 25, the surface of the PVDF membrane 60 adjacent the reservoir 25 is laminated with an ultrafiltration membrane 65 consisting of any biocompatible material with pore sizes of less than 1.0 µm. Preferably, the ultrafiltration membrane is constructed using a hydrogel of photopolymerized polyethylene glycol (PEG). The molecular weight of the PEG membrane may range in size from 100 Da to 50 Kda or more preferably 575 Da. (Sigma Chemical). In one embodiment, the laminated filtration membranes 10 are formed by spin coating aqueous hydrogel precursor solutions on the inside of the PVDF membrane 60 (e.g., a precursor solution consisting of 23% PEG-dacrylate and 0.1% 2,2'-dimethoxy-2Diphenylacetophenone (Sigma Chemical Part # 24650-42-8), a UV-activated free radical polymerization agent). The high viscosity of the solution and surface tension between the PVDF membrane and the precursor solution does not allow significant solution penetration into the pores of the PVDF membrane and therefore does not inhibit neovascularization. The coated PVDF membrane 60, is then illuminated by UV light (e.g., 365 nm, 20 mW/cm$^2$) at a distance of approximately 1 cm until complete polymerization has taken place (typically two to ten seconds or less). The filtration membrane 10 is then attached to the housing 15 using a medical grade adhesive (e.g., an epoxy such as Loctite # 4981).

In one embodiment, the PVDF membrane 60 has a pore size ranging from 0.05 µm to 40 µm, preferably about 5 µm. The thickness of the filtration membrane 10 preferably may range from 10 µm to 500 µm, and even more preferably is about 100 µm. The diameter of the filtration membrane 10 preferably ranges from 0.1 to 3.0 cm in diameter, and even more preferably is about 0.7 cm.

In short, the filtration membrane is designed to promote neovascularization on the tissue interfacing side while preventing cellular passage with a bioprotective layer on the device side. As mentioned above, PEG is preferable but many materials with pore sizes too small for cells to pass through may be used. In addition, as mentioned above, photopolymerized PEG is suitable but other techniques of polymerization of the PEG are acceptable, for example, thermal or chemical methods may be used to initiate polymerization of the PEG.

Implant Housing

Figure 1E:
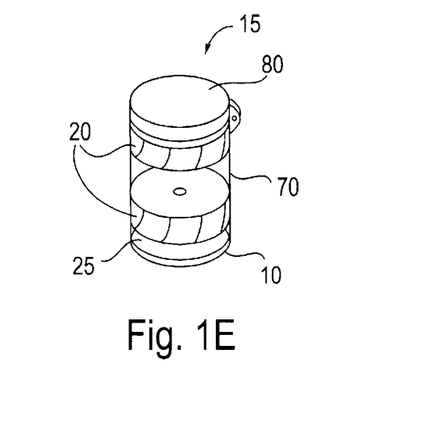
FIG. 1E is an elevational perspective side view of the housing component which contains safety valves and a reservoir of one embodiment of the present invention.

As depicted in FIG. 1E, central housing 15 includes a conduit 70 with septa 20 contained within conduit 70. The distal end of conduit 70 is sealed with filtration membrane 10. The portion of conduit 70 between the top of filtration membrane 10 and the bottom of lower septum 20 form collection reservoir 25. The top of conduit 70 contains a cap 80 to prevent debris and contaminants from entering conduit 70 when implantable access port 1 is not in use. Although cap 80 depicted in FIG. 1E is a hinged, spring-loaded cap, numerous other cap designs may be used including, without limitation, a removeable, snap-on or screw on cap.

The conduit 70 is preferably formed of stainless steel tubing or other rigid biocompatible material. Alternatively, conduit 70 may be formed integrally with housing 15, being defined by the lumen thereof. The outer diameter of housing 15 may range from 0.1 to 2.0 cm, and is preferably about 0.7 cm. The lumen diameter of housing 15 may range from 0.125 to 1.775 cm, and is preferably about 0.5 cm. Each of septum 20 is preferably constructed of an elastic, self-sealing biocompatible material, more preferably silicone rubber and is sized to fit snugly within the lumen of conduit 70, thus providing a liquid-tight seal between collection reservoir 25 and the upper portion of conduit 70. The thickness of the individual septum 20 preferably may range from 0.05 to 1.0 cm and more preferably is about 0.3 cm. The distance between the bottom of lower septum 20 and filtration membrane 10 defines the depth of collection reservoir 25 and preferably may range from 0.05 cm to 2.0 cm and more preferably is about 0.2 cm. The resulting volume of collection reservoir 25 may range from 0.6 µl to 5.0 ml and more preferably is about 40 µl.

Figure 2A:
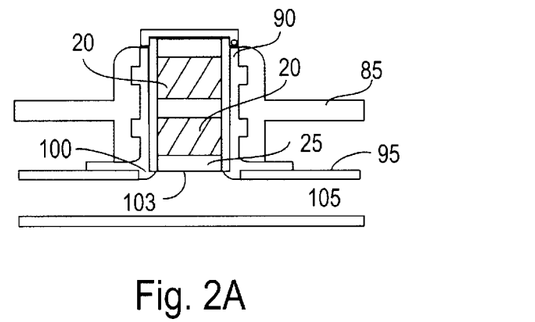
FIG. 2A is a cross-sectional view of another embodiment of an implantable access port for access to the blood space in accordance with the present invention.

FIG. 2A illustrates an alternative embodiment of an implantable access port designed to be used for filtration of blood components. The implant includes a transcutaneous access component 85 with a central housing component 90 connected to an arterio-venous shunt 95. The distal end of the housing component 100 is secured to the wall of the arterio-venous shunt such that an appropriate filtration membrane 103 resides within the lumen of the arterio-venous shunt 105. Blood flowing through the arterio-venous shunt 95 is thereby filtered by the filtration membrane 103 and fluid is subsequently collected through the housing 90.

Figure 2B:
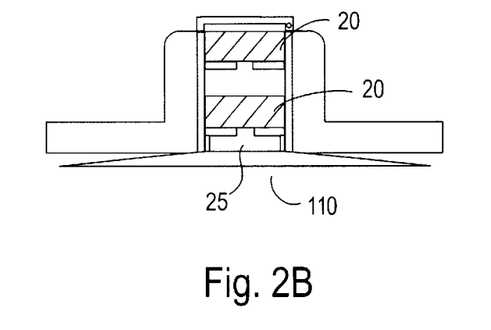
FIG. 2B is a cross-sectional view of another embodiment of the access port that includes a specially shaped filtration membrane to enhance mass transfer.

FIG. 2B illustrates a further embodiment of an implantable access port described above modified such that the filtration membrane 110 is shaped to increase the surface area and hence mass transport between the tissue space and collection reservoir of analytes in interstitial fluid, blood, or blood plasma.

Figure 2C:
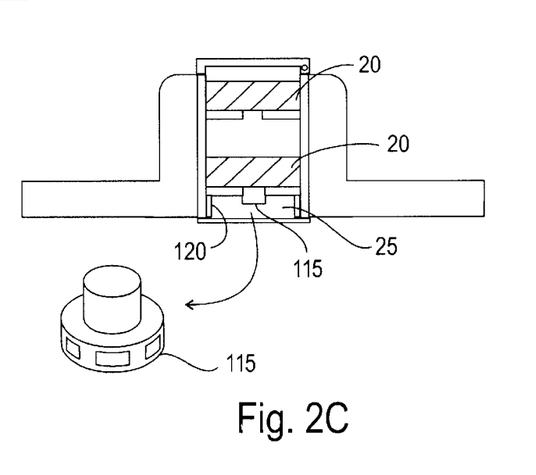
FIG. 2C is an elevational side view of another embodiment of the access port in which a safety stop is included within the reservoir to prevent damage to the filtration membrane and the reservoir is coated with an antibacterial agent.

FIG. 2C illustrates a further embodiment of the collection reservoir in which a safety stop 115 is incorporated to prevent the aspirating device such as needles or capillary tubes from damaging the filtration membrane and a coating of silver 120 is used to prevent bacterial accumulation in the collected fluid. As shown in FIG. 2C, the safety stop includes apertures along its circumference to permit analyte to pass in either direction between the reservoir and the aspirating device (or an agent delivery device). Preferably, the aspirating or delivery device having a side opening to the fluid intake or exhaust port to avoid blockage when the tip of the aspirating or delivery device contacts the bottom of the safety stop. In an alternative embodiment, apertures smaller than the tip of the aspirating or agent delivery device may be distributed throughout the surface of the safety stop, permitting a fluid intake or exhaust port to be located anywhere on the aspirating or agent delivery device, including on the bottom of its tip.

Figure 2D:
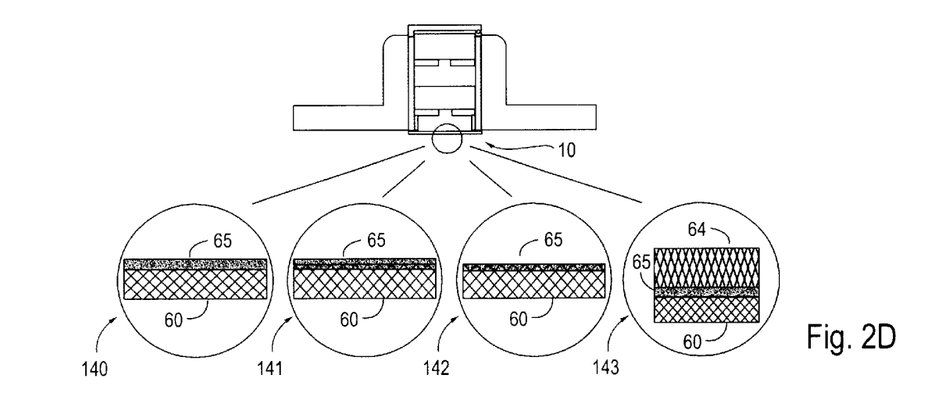
FIG. 2D is a cross-sectional view of another embodiment of the access port of the present invention.

FIG. 2D is a cross-section of the implantable access port shown in FIG. 1A demonstrating alternative configurations for layers contained in the advanced filtration membrane 10. The advanced filtration membrane 10 may be composed of a discrete two-layer filtration membrane 140. In this configuration the PVDF membrane 60 is coated with a discrete layer of PEG membrane 65. Alternatively the advanced filtration membrane 10 may be composed of a partially embedded 2-layer filtration membrane 141 in which the PEG ultrafiltration membrane 65 partially penetrates a small distance into the PVDF membrane 60. In another alternative, the advanced filtration membrane 10 may be composed of a fully embedded 2-layer filtration membrane 142. In this configuration the full thickness of the PEG ultrafiltration membrane 65 is contained within a thickness of the PVDF membrane 60. In yet another alternative, the advanced filtration membrane 10 may be composed of a three layer filtration membrane 143. In this configuration a membrane support screen 64 is included to provide additional support to the filtration membrane 10. The membrane support screen may consist of any semi-rigid or rigid material but is preferably made using a stainless steel screen.

Figure 2E:
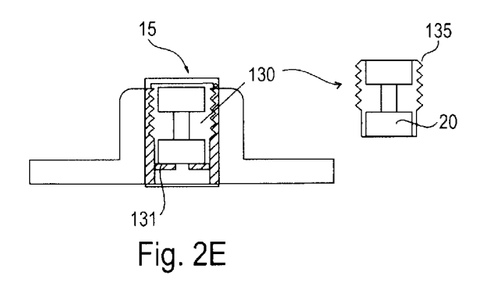
FIG. 2E is a cross-sectional view of yet another embodiment of the access port of the present invention.

FIG. 2E is a cross-section of the implantable access port shown in FIG. 1A demonstrating alternative configurations for the housing 15 in which a replaceable septa insert 130 is incorporated. In this embodiment, the septa 20 are contained within a replaceable insert 130. The replaceable insert 130 may contain a threaded wall 135 such that once the septa 20 become worn to the point that they no longer self-seal, the user may unscrew the insert 130 and replace it with a new one. The new septa insert 130 is screwed into the threaded wall of the housing until it abuts a stop wall 131, thus allowing the inert 130 to be properly disposed within the lumen of the housing 15 (or conduit as shown in FIG. 1E). Other mechanisms for securing the replaceable insert may also be used including, without limitation, friction holds, mechanical catches and the like.

Figure 2F:
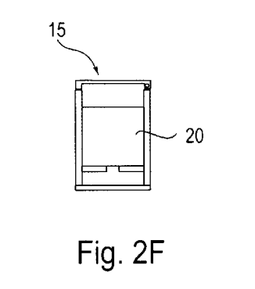
FIG. 2F is a cross-sectional view of another embodiment of the access port of the present invention.

FIG. 2F is a cross-section of the housing 15 in which only a single self-sealing septum 20 is used. Any of the alternative embodiments may contain a single self-sealing septum 20 as opposed to the two-septum configuration as shown in FIG. 1B.

Figure 3A:
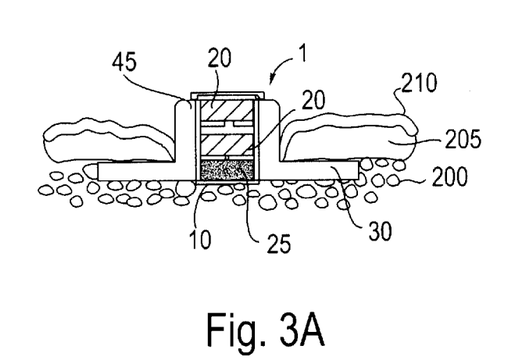
FIG. 3A illustrates a side view of the access port of the present invention which has been implanted.

Turning to the operation of the preferred embodiment of the present invention, referring to FIG. 3A, implantable access port 1 is implanted so that skirt 30 of access component 5 is anchored in subcutaneous tissue 200 and neck 45 of access component 5 penetrates dermal 205 and epidermal layer 210 of the skin. After implantation, fibrous collagen begins to deposit in holes 40 in skirt 30 to help anchor access component 5. The velour covering 55 provides a porous, fibrous-structure bed to encourage the growth of tissue and collagen around skirt 30 to provide a biological seal with the epidermal cells which migrate and invaginate along neck 45 until they reach the covering.

The housing component 15, which is fixed within access component 5, provides for collection of fluid from the body without requiring breaking the skin barrier. The filtration membrane 10 attached to housing 15 allows passage of interstitial fluid, blood, or blood plasma while preventing larger cells and proteins from entering collection reservoir 25. The fluid filtered by membrane 10 and stored in collection reservoir 25 becomes the sample for analyte measurement using any applicable small volume sensor.

Figure 3B:
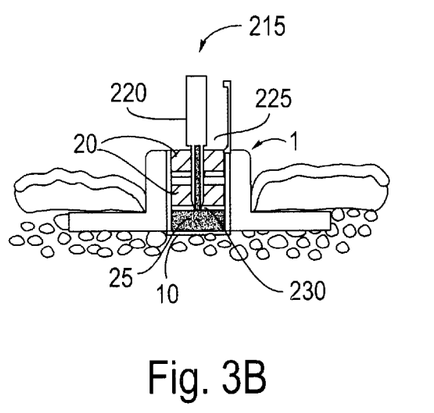
FIG. 3B illustrates a side view of the access port of the present invention which has been implanted and is in use with a device for collection or delivery of fluid.

In the preferred embodiment, as shown in FIG. 3B, implantable access port 1 is designed to be used in conjunction with a sampling device 215. The sampling device 215 may be a needle or catheter, but is preferably a specially designed capillary tube 220 with an integral stop 225 such that it cannot be introduced far enough to damage filtration membrane 10. The sampling device 215 is passed through the self-sealing septa such that the distal end of sampling device 230 is positioned within collection reservoir 25 but does not come in contact with filtration membrane 10. Fluid is drawn within a collection chamber of sampling device 215 by capillary action or aspirating the proximal end of sampling device 215 (e.g., by slideably withdrawing a plunger from the chamber of sampling device 215).

Alternatively the implantable access port described herein may be used to deliver agents into the body. Such agents might include, but are not limited to, drugs, hormones, chemotherapeutic agents, photosensitizing agents, vaccines, radiological, or contrast agents. In operation, the agent to be administered would be placed within the collection reservoir 25 (now being used as a delivery reservoir) and the membrane 10 would be designed to allow passage of the agent into the subcutaneous fluid or blood space. Of particular interest, is the operation of the implantable access port to deliver insulin or for use in combination with insulin pumps.

The implantable access port described herein may be implanted anywhere on the body having a soft tissue layer sufficiently thick to accommodate the protrusion of the access port into the subdermal space. Preferably the implant is placed on the wrist or arm area for easy patient access and may include a device or implement to cover the port such as a wrist watch interface or skin colored bandage to improve patient acceptance of the aesthetic qualities of the device. Further, for durability, the access port is preferably placed somewhere on the body which is not subject to a lot of exposure or contact such as the abdomen.

As seen from the foregoing, the implantable access port provides a method for withdrawal of body fluids without requiring breach of the skin barrier. The implantable access port also provides for filtration of interstitial fluid, blood, or blood plasma resulting in a sample of fluid containing an analyte of interest. Because of its porosity and fibrous structure, the access port forms an infection-free, transcutaneous implant having a biological seal around the device. Therefore, the implant is suitable for long term use. Since the implant resides in the plane between the subcutaneous and dermal layers of tissue, subsequent removal is simple if necessary. Additionally, the access port has relatively few components and may be easily manufactured with common, readily available materials. Once implanted, the withdrawal of fluid from the body can be performed in a painless and reliable manner.

Figure 4A:
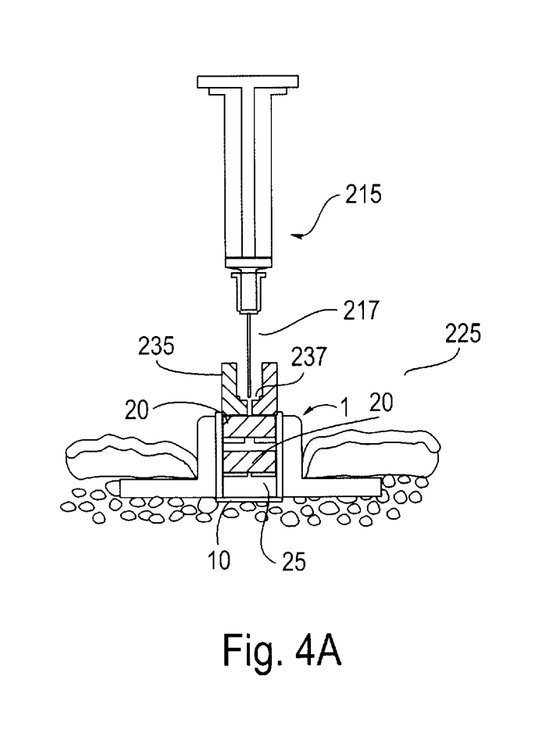
FIG. 4A illustrates a side view of an implanted access port according to an embodiment that includes an external sampling stop.
Figure 4B:
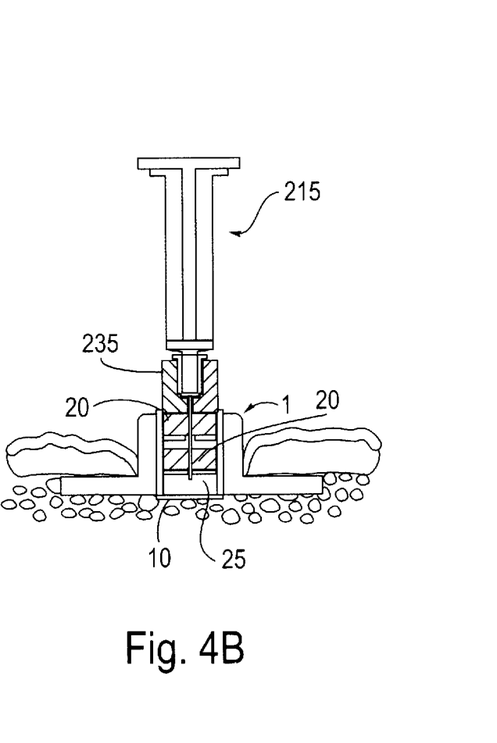
FIG. 4B illustrates insertion of a sampling device that includes a needle into the implanted access port of FIG. 4A.

FIG. 4A illustrates a side view of an embodiment of an implanted access port which includes an external sampling stop 235 for providing safe access to the interstitial fluid without damaging the filtration membrane 10. As shown in FIG. 4B, the external sampling stop 235 permits a needle 217 to be used with the sampling device 215 in a safe manner. The sampling device 215 is inserted into the external sampling stop 235 until a flange at the forward end of the sampling device abuts a stop wall 237. As the sampling device 215 is inserted into the sampling stop 235, the needle 217 extends through an aperture in the stop wall 237, passes through the self-sealing septa 20 and comes to rest with the tip located just within the reservoir 25. The needle is preferably a non-coring needle (Part No. 7165, Popper & Sons, Inc., New Hyde Park, N.Y.) to prevent coring of the self-sealing septa 20. The sampling stop 235 can be custom designed according to the needle 217 and sampling device 210 used. In one embodiment, the sampling stop is removable, for example by unplugging or unscrewing from the implant 1, thus permitting sampling stops having various profiles and receptacle shapes to be used interchangeably. In an alternative embodiment, the sampling stop 235 forms part of the implant and is capped by an end cap as discussed above (see, for example, FIG. 1E, element 80).

Figure 5A:
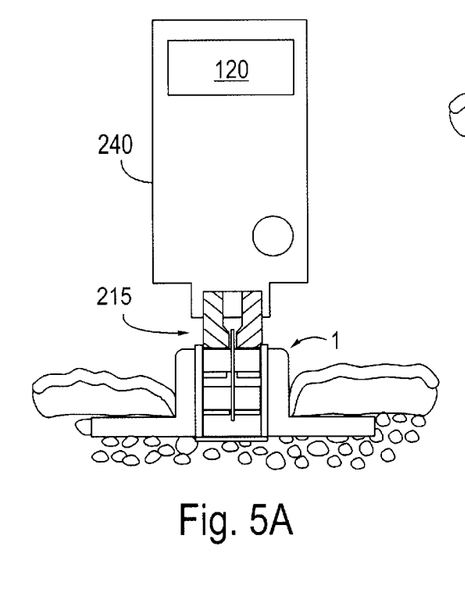
FIG. 5A illustrates a side view of an implanted access port used in conjunction with an external analyte measurement device.

FIG. 5A illustrates a side view of the implanted access port used in conjunction with an external analyte measurement device. In this embodiment an external analyte measurement device 240 is interfaced with the sampling device 215. This configuration allows for interstitial fluid withdrawn from the device and containing the analyte of interest to be directly communicated to an external analyte measurement device 240.

Figure 5B:
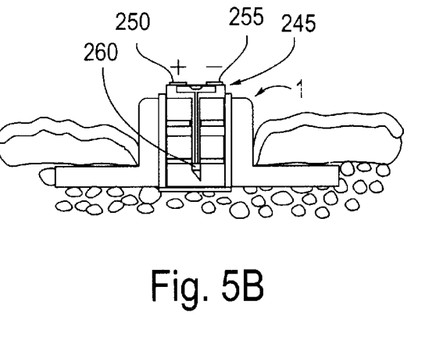
FIG. 5B illustrates a side view of an implanted access port according to an embodiment that includes a replaceable electro-enzymatic sensor.
Figures 5C, 5D:
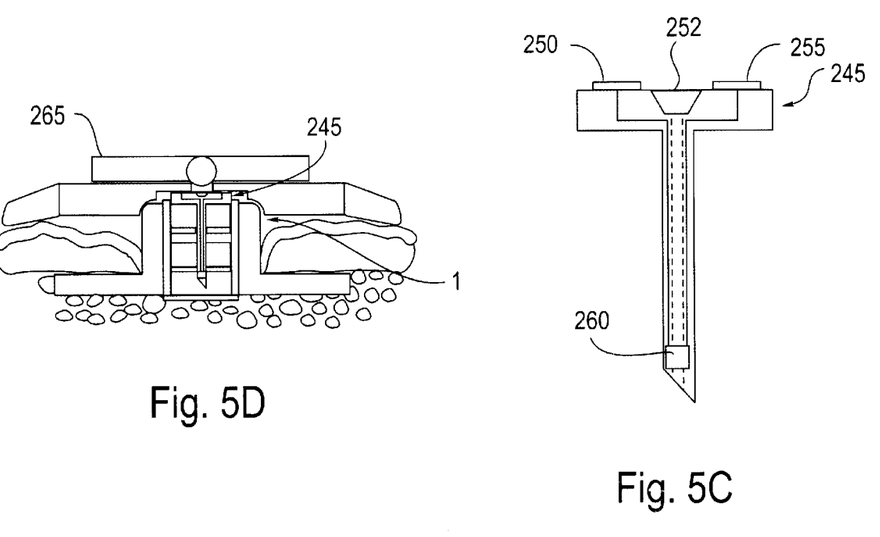
FIG. 5C illustrates a side view of the replaceable sensor included in the implanted access port of FIG. 5B.
FIG. 5D illustrates the implantable access port and replaceable electroenzymatic sensor of FIG. 5B used in conjunction with a wristwatch style measurement device.

FIG. 5B illustrates a side view of an implanted access port that incorporates a replaceable electro-enzymatic sensor 245. In one embodiment, the sensor chemistry 260 is contained with the electroenzymatic sensor 245 and is placed within the reservoir 25 containing the interstitial fluid. Such a sensor chemistry is described in detail by Quinn et al. (Photo-crosslinked copolymers of 2 hydroxyethyl methacrylate, poly(ethylene glycol) tetra-acrylate and ethylene dimethacrylate for improving biocompatibility of biosensors), the entire content of which is hereby incorporated by reference. In the embodiment shown in FIG. 5B, a working electrode terminal 250 and a reference electrode terminal 255 are incorporated on the replaceable sensor 245 such that they are located outside the access port 1 with electrical conductors that are connected with the sensor chemistry 260. By this arrangement, an external analyte measurement device 240 may be interfaced with the replaceable sensor 245 to provide a measurement of the analyte of interest. FIG. 5C illustrates a close up side view of the replaceable sensor 245. The sensor 245 may also contain a fluid withdrawal port 252 that would allow the user to withdraw interstitial fluid periodically in,order to calibrate the electroenzymatic sensor 245. Alternatively, the sensor 245 can be removed from the access port 1 and calibrated in known standards.

FIG. 5D illustrates implantable access port 1 and replaceable electroenzymatic sensor 245 of FIG. 5B used in conjunction with a wristwatch style measurement display device. In this embodiment, a wristwatch style analyte measurement display device 265 may be continuously worn over implantable access port 1 and replaceable electroenzymatic sensor 245 to display continuous measurement of the analyte of interest. Numerous other styles and configurations of measurement display devices may be worn over implantable access port 1 in alternative embodiments.

While the present invention has been described with reference to illustrative embodiments that include specific details, such embodiments and details should not be construed as limiting the scope of the invention. For example, though numerous preferences for shapes, materials, sizes and configurations have been described, other 20 shapes, materials, sizes and configurations may be used without departing from the spirit and scope of the present invention. Those having ordinary skill in the art and access to the teachings provided herein will recognize additional modifications, applications, and embodiments within the scope the invention described herein and additional fields in which the invention would be of significant utility without undue experimentation. Thus the scope of the invention should be determined by the appended claims and their legal equivalents, rather than by the examples given.

What is claimed is:

1. A transcutaneous implant comprising:
   an access component to provide a stable dermal interface;
   a central housing disposed within the access component, the central housing having a first end for external access and a second end;
   a first septum disposed within the central housing; and
   a filtration membrane disposed at the second end of the central housing to allow analyte in bodily fluid to enter a reservoir formed by the filtration membrane, the first septum and the central housing, wherein the filtration membrane includes a first material to promote neovascularization.

2. The implant of claim 1 wherein the access component includes a neck having a first end and a second end, and skirt that extends outwardly from the second end of the neck to anchor the access component in subcutaneous tissue.

3. The implant of claim 2 wherein the central housing is formed integrally with the access component and is defined by an inner surface of the neck.

4. The implant of claim 2 wherein the central housing extends beneath the skirt of the access component and is adapted to be secured to a wall of an arterio-venous shunt such that the filtration membrane resides within the arterio-venous shunt.

5. The implant of claim 2 wherein the access component includes a porous material disposed on at least a portion of the skirt of the access component wherein the porous material encourages cell infiltration and formation of tissue.

6. The implant of claim 5 wherein the porous material includes polyester velour.

7. The implant of claim 2 wherein the skirt and neck are integrally formed of a flexible, biocompatible material.

8. The implant of claim 7 wherein the flexible biocompatible material is a member of a group of materials that includes flexible medical grade polyurethane, polymethyl methacrylate (PMMA), polyethylene (PE), polyvinyl chloride (PVC), polycarbonate, polypropylene (PP) polydimethyl siloxane (PDMS), ethylene glycol dimethacrylate (EGDM), polytetrafluoroethylene PTFE), and nylon.

9. The implant of claim 2 wherein the skirt includes recessed regions containing a material that encourages growth of fibrous collagen, wherein the fibrous collagen promotes a stable seal between the access component and the skin.

10. The implant of claim 1 wherein the filtration membrane includes a material that allows passive diffusion of the analyte in the bodily fluid and substantially prevents transport of cells or larger proteins.

11. The implant of claim 1 wherein the first material is at least one of cellulose acetate, mixed esters of cellulose, polysulfone, polyester, polypropylene, cellulose nitrate, polycarbonate nylon, polyethylene, and vinyl acetate ethylene copolymers.

12. The implant of claim 1 wherein the first material includes polyvinylidene fluoride (PVDF).

13. The implant of claim 1 wherein the filtration membrane further includes a second material which allows passive diffusion of the analyte in the bodily fluid and substantially prevents transport of cells or larger proteins.

14. The implant of claim 13 wherein the second material includes polymerized polyethylene glycol (PEG).

15. The implant of claim 13 wherein the second material is laminated on the first material to form a two-layer filtration membrane.

16. The implant of claim 13 wherein a portion of the second material penetrates into the first material to form a partially embedded two-layer filtration membrane.

17. The implant of claim 13 wherein the second material is contained within a layer of the first material to form an embedded two-layer filtration membrane.

18. The implant of claim 13 wherein the filtration membrane further includes a third material, which is more rigid than at least one of the first material and the second material, to provide support to the filtration membrane.

19. The implant of claim 1 wherein the first material has a pore size ranging from 0.05 $\mu$m to 40 $\mu$m.

20. The implant of claim 1 wherein the first septum forms a liquid-tight seal between the reservoir and a side of the first septum nearest the first end of the central housing.

21. The implant of claim 20 wherein the first septum is formed of a self-sealing material such that, after the first septum has been penetrated by a fluid sampling/delivery device and the fluid sampling/delivery device removed, the first septum self-seals to reestablish the liquid-tight seal.

22. The implant of claim 21 wherein the first septum is formed from a material that includes silicone rubber.

23. The implant of claim 1 wherein the central housing includes a conduit disposed within the lumen of the central housing and wherein the first septum is disposed within the conduit and the filtration membrane is disposed at an end of the conduit adjacent the second end of the central housing.

24. The implant of claim 23 wherein the conduit is formed integrally with the central housing, the conduit being defined by an inner surface of the central housing.

25. The implant of claim 23 wherein the conduit is formed of a rigid biocompatible material.

26. The implant of claim 23 further comprising a cap disposed over an end of the conduit adjacent the first end of the central housing.

27. The implant of claim 23 further comprising a second septum disposed within the conduit nearer the first end of the central housing than the first septum, the first and second septa defining a chamber within the conduit.

28. The implant of claim 23 further comprising a support member disposed within the conduit to support the first septum, the first septum being disposed within the conduit adjacent the support member.

29. The implant of claim 1 further comprising a cap disposed over the first end of the central housing.

30. The implant of claim 1 further comprising a second septum disposed within the central housing nearer the first end than the first septum, the first and second septa defining a chamber within the central housing.

31. The implant of claim 30 where in the second septum forms a liquid-tight seal between the chamber and a side of the second septum nearest the first end of the central housing.

32. The implant of claim 1 wherein the filtration membrane is attached to the central housing using a medical grade adhesive.

33. The implant of claim 1 wherein the filtration membrane extends outwardly to form a surface area that exceeds an area of a cross section of the second end of the central housing.

34. The implant of claim 1 further comprising a safety stop to prevent a fluid sampling/delivery device from contacting the filtration membrane.

35. The implant of claim 34 wherein the safety stop is disposed within the reservoir, the safety stop including an aperture to permit the analyte to pass between the reservoir and the fluid sampling/delivery device.

36. The implant of claim 1 wherein at least a portion of the reservoir is lined with an antibacterial coating.

37. The implant of claim 36 wherein the antibacterial coating includes silver.

38. The implant of claim 1 wherein the first septum is removable from the central housing to allow replacement thereof.

39. The implant of claim 1 further comprising a sampling stop disposed at the first end of the central housing to limit the insertion of a fluid sampling/delivery device such that the device is prevented from contacting the filtration membrane.

40. The implant of claim 39 wherein the sampling stop includes a stop wall adapted to engage a flange of the fluid sampling/delivery device, the stop wall including an aperture to receive a narrower portion of the fluid sampling/delivery device such that a tip of the narrower portion of the fluid sampling/delivery device rests within the reservoir when the flange of the fluid sampling/delivery device engages the stop wall.

41. The implant of claim 39 wherein the sampling stop is removable from the implant.

42. The implant of claim 1 wherein the central housing is adapted to engage an analyte measurement device and fluid sampling device such that the analyte in the reservoir is communicated to the analyte measurement device via the fluid sampling device and measured by the analyte measurement device while the analyte measurement device and fluid sampling device are engaged by the central housing.

43. A sensing system having a transcutaneous implant device comprising:
   an electroenzymatic sensor;
   a transcutaneous implant device, including:
      an access component to provide a stable dermal interface;
      a central housing disposed within the access component, the central housing having a first end for external access and a second end;
      a first septum disposed within the central housing; and
      a filtration membrane disposed at the second end of the central housing to allow analyte in bodily fluid to enter a reservoir formed by the filtration membrane, the first septum and the central housing, wherein the filtration membrane includes a first material to promote neovascularization.

44. The sensing system of claim 43 wherein the electroenzymatic sensor includes a chemical sensor disposed within the reservoir and first and second terminals disposed adjacent the first end of the central housing and coupled to the chemical sensor via respective electrical conductors.

45. The sensing system of claim 43 wherein the electroenzymatic sensor further includes a fluid withdrawal port to allow periodic withdrawal of the analyte.

46. The sensing system of claim 43 wherein the electroenzymatic sensor is removable.

47. The sensing system of claim 43 further comprising a display device coupled adjacent the first end of the central housing, the display device cooperating with the electroenzymatic sensor to display a measure of the analyte.

48. The sensing system of claim 47 wherein the display device is a wristwatch style device.

49. An implant to deliver fluid to, withdraw fluid from, or monitor a fluid of an animal body, the implant comprising:
   an access component to provide a stable dermal interface wherein the access, component includes a housing having a first end which is externally accessible, capable of being without puncturing the skin of the animal body and a second end;
   a septum, disposed within the housing, to provide a liquid tight seal; and
   a membrane disposed at, and coupled to the second end of the housing wherein the membrane includes a first material that promotes neovascularization when located within the animal body and wherein the membrane, the septum and the housing form a reservoir.

50. The implant of claim 49 wherein the first material is at least one of cellulose acetate, mixed esters of cellulose, polysulfone, polyester, polypropylene, cellulose nitrate, polycarbonate nylon, polyethylene, and vinyl acetate ethylene copolymers.

51. The implant of claim 49 wherein the membrane further includes a second material which allows fluid to diffuse therethrough and substantially prevents cells from entering the reservoir.

52. The implant of claim 51 wherein the second material is laminated onto the first material to form a two-layer membrane.

53. The implant of claim 51 wherein the second material is contained within a layer of the first material to form an embedded two-layer membrane.

54. The implant of claim 51 wherein the first material includes a pore size ranging from 0.05 $\mu$m to 40 $\mu$m.

55. The implant of claim 51 further including a safety stop to prevent a fluid sampling/delivery device from contacting the membrane.

56. An implant to deliver fluid to, withdraw fluid from, or monitor a fluid of an animal body, the implant comprising:

an access component to provide a stable dermal interface wherein the access component includes a housing having a first end which is externally capable of accessible without puncturing the skin of the animal body and a second end;

a septum, disposed within the housing, to provide a liquid tight seal; and a membrane disposed at, and coupled to the second end of the housing wherein the membrane includes a first material that retards avascularization when located within the animal body and wherein the membrane, the septum and the housing form a reservoir.

57. The implant of claim 56 wherein the first material includes a pore size ranging from 0.05 $\mu$m to 40 $\mu$m.

58. The implant of claim 57 wherein the membrane further includes a second material which allows fluid to diffuse therethrough and substantially prevents cells from entering the reservoir.

* * * * *